United States Patent [19]

Fruchey

[11] Patent Number: 4,910,338

[45] Date of Patent: Mar. 20, 1990

[54] PRODUCTION OF α-CHLORO-α-OXIMINO-4-HYDROXYACETOPHENONE

[75] Inventor: Olan S. Fruchey, Corpus Christi, Tex.

[73] Assignee: Hoechst Celanese Corporation, Sommerville, N.J.

[21] Appl. No.: 311,548

[22] Filed: Feb. 14, 1989

[51] Int. Cl.$^4$ .............................................. C07C 83/10
[52] U.S. Cl. ..................................... 562/800; 564/258
[58] Field of Search .................. 560/543 A; 564/258; 562/800

[56] References Cited

U.S. PATENT DOCUMENTS

| | | | |
|---|---|---|---|
| 1,995,710 | 3/1935 | Hartung | 260/128.5 |
| 2,844,630 | 7/1958 | Johnson et al. | 564/258 |
| 3,090,812 | 5/1963 | Wilbert et al. | 260/566 |
| 3,697,596 | 10/1972 | Dorlars | 260/465 |
| 3,966,813 | 6/1976 | Satzinger et al. | 260/570.6 |

FOREIGN PATENT DOCUMENTS 1290646 9/1972 United Kingdom .

OTHER PUBLICATIONS

Brachwitz et al, Chem Abst., vol. 67, #90534n (1967).
Brachwitz et al, Chem. Abst., vol. 65, #16891a (1966).
Singhal et al, Chem Abst., vol. 55, #27186a (1961).
Shevchuk et al, Chem. Abst., vol. 75, #63350h (1971).
*Annalen der Chemie*, "On the Reaction of Nitrosyl Chloride–'nitrosyl Chlorination' by means of Nitrosyl Chloride", Heinrich Rheinboldt and Otto Schmitz-Dumont, vol. 444, pp. 113–135, (1925).
*Journal of the Organic Chemistry*, "Amino Alcohols, XI. Arylglyoxylohydroxamyl Chlorides", Nathan Levin and Walter E. Hartung, vol. 7, pp. 408–415, (1942).
*Journal of the Organic Chemistry*, "Action of Nitrosyl Chloride on Oximino Esters", L. W. Kissinger and H. E. Ungnade, vol. 23, pp. 1517–1518, (1958).
*Zeitschrift, Fur Chemie*, "On the Preparation of alpha--chloro-alpha-isonitrosoacetophenones", vol. 6, No. 8, pp. 313–314, (1966).

Primary Examiner—James H. Reamer
Attorney, Agent, or Firm—Donald R. Cassady

[57] ABSTRACT

α-chloro-α-oximino-4-hydroxyacetophenone is prepared by reacting 4-hydroxyacetophenone with an alkyl nitrite and hydrogen chloride wherein the amount of hydrogen chloride is carefully controlled to limit the amount thereof to about 0.1 to 6 moles of hydrogen chloride per mole of 4-hydroxyacetophenone until at least one equivalent of the alkyl nitrite is reacted. Subsequent to the reaction of the one equivalent of alkyl nitrite, at least 1 mole of hydrogen chloride per mole of initially charged 4-hydroxyacetophenone is added to the reaction medium.

20 Claims, No Drawings

PRODUCTION OF α-CHLORO-α-OXIMINO-4-HYDROXYACETOPHENONE

BACKGROUND OF THE INVENTION

The present invention is directed to a novel process for the production of α-chloro-α-oximino-4-hydroxyacetophenone.

α-chloro-α-oximino-4-hydroxyacetophenone is known and has the structural formula (I):

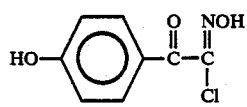

The preparation thereof has been described in the literature, for example, by N. Levin and W. H. Hartong, *Journal of Organic Chemistry*, (1942), 7,408. Preparation involves reacting hydroxyphenacyl chloride with isopropyl nitrite in the presence of hydrogen chloride to yield the product. The reaction can be depicted as in equation (II):

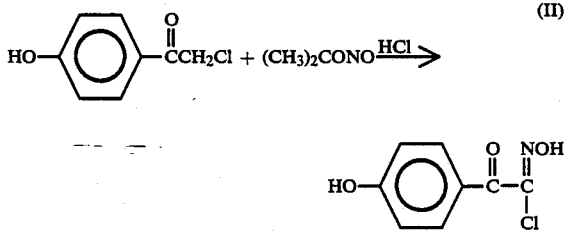

α-chloro-α-oximino-4-hydroxyacetophenone is known to have good antibacterial and germicidal properties. Thus, the compound has found use as an industrial biocide to control the growth of bacteria and microorganisms which develop in water-based media used in the manufacture of various industrial products. Discovery of the antibacterial and germicidal properties of α-chloro-α-oximino-4-hydroxyacetophenone is described in British Pat. No. 1,290,646. For use as an industrial biocide, the active ingredient is used in association with a suitable vehicle. Suitable vehicles include water, alcohols, hydrocarbons and other organic solvents as well as mineral, animal and vegetable oils. The compositions typically contain upwards of 10–20% by weight of the active ingredient.

While the previous method of forming α-chloro-α-oximino-4-hydroxyacetophenone has been useful, the starting hydroxyphenacyl chloride is disadvantageous in view of its cost and, because it is a solid, it is difficult to handle. Also, hydroxylphenacyl chloride is a strong lachrymater and causes severe dermatitis.

Accordingly, it would be worthwhile to provide a new process for the production of α-chloro-α-oximino-4-hydroxyacetophenne, in particular, a process that would use a starting material which is less expensive and easier to handle than hydroxyphenacyl chloride. Thus, the primary objective of the present invention is to provide such a novel process for the production of α-chloro-α-oximino-4-hydroxyacetophenone.

SUMMARY OF THE INVENTION

The present invention is directed to a novel process for the production of α-chloro-α-oximino-4-hydroxyacetophenone. This compound can be formed and then incorporated into a liquid vehicle for use as an effective biocide composition.

The novel process of the present invention involves forming α-chloro-α-oximino-4-hydroxyacetophenone by the reaction of 4-hydroxyacetophenone (4-HAP) with isopropyl nitrite and a controlled amount of hydrogen chloride to provide the product in good yields and with good purity. The important feature of the present invention is to limit the amount of hydrogen chloride provided in the reaction medium during the initial stages of the reaction, i.e., while the first equivalent of isopropyl nitrite is being reacted. It has been found that if large amounts of hydrogen chloride are present initially such as by continual sparging through the reaction medium from the beginning of reaction, low yields of the desired product are obtained and undesirable side products are produced.

DETAILED DESCRIPTION OF THE INVENTION

The process for producing α-chloro-α-oximino-4-hydroxyacetophenone (CHIMP) in accordance with the present invention comprises reacting 4-hydroxyacetophenone with an alkyl nitrite and hydrogen chloride in which the presence of hydrogen chloride is controlled to limited amounts during the initial stage of the reaction in order to yield a high purity product at good yields. The product can then be added to a vehicle for use as a biocide composition.

The 4-hydroxyacetophenone used as the starting material may be prepared by any method known in the art. For example, it may be prepared by the Fries rearrangement of the corresponding aromatic ester, e.g., phenyl acetate as indicated by the following equation where Ar is phenyl, Ar$^1$ is 1,4phenylene and R is methyl:

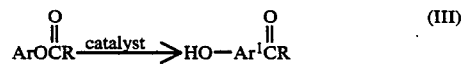

Alternatively, phenol and an acylating agent may be reacted in a Friedel-Crafts acylation to form hydroxy acetophenone in accordance with the following equation:

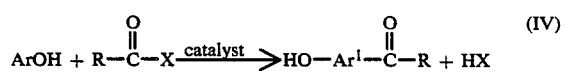

where Ar, Ar$^1$ and R have the meanings previously and X is the residue minus the acyl group,

of the compounds which are known acylating agents, such as hydroxy, acyloxy, e.g. acetoxy, and halide, e.g., fluoride, chloride, bromide, and iodide. Acylating agents which may be used are, for example, acetic acid, acetic anhydride, and acyl halides, e.g., aacetyl fluoride, chloride, and bromide. Note that although the reaction of phenol add an acylating agent is characterized herein as a "Friedel-Crafts acylation," no opinion as to the mechanism of reaction should be implied by this characterization.

The catalyst for both of the foregoing reactions is preferably hydrogen fluoride but ny other catalyst known in the art to be effective for the Fries and Friedel-Crafts reactions may be used, e.g., aluminum chloride, zinc chloride, or boron trifluoride.

In carrying out the reaction, phenyl acetate or phenol and acylating agent, catalyst and if desired when phenyl acetate is the starting material, an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at pressure, for example, of about 50 to about 500 psia. If HF is used as the catalyst it ay be charged as a liquid or a gas using technologies of handling well-known to those skilled in the art. In carrying out the reaction, an inert gas such as nitrogen may be used to be the reaction space under the desired pressure and sufficient HF in contact with the reacting liquid. An excess of HF is generally used, for example, about 7 to about 75 moles per mole of phenyl acetate or phenol initially present in the reaction zone. In both cases, the starting material is converted to 4-HAP which is in turn converted by the process of this invention to CHIMP.

The formation of 4-HAP is more fully described in U.S. Pat. No. 4,568,763 herein incorporated by reference.

The conversion of 4-HAP to α-chloro-α-oximino-4HAP can be depicted as a two-stage reaction procedure as shown in equations (V) and VI).

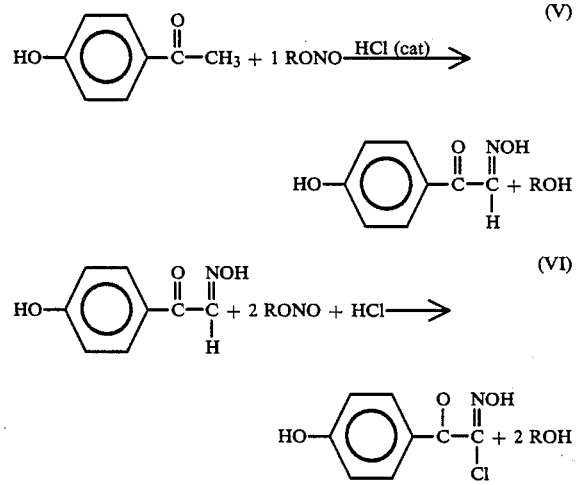

where R is an alkyl containing 1 to 4 carbon atoms. Useful alkyl nitrites include, for example, methyl nitrite, ethyl nitrite, n-butyl nitrite and the like. Preferably, isopropyl nitrite is used. When the higher boiling, normally liquid organic nitrites such as isopropyl nitrite are utilized, the organic nitrite is supplied dropwise to the reaction medium which contains the 4-HAP in an appropriate solvent. Any appropriate solvent can be used to dissolve the 4-HAP, including ethers, alcohols, etc. Ethers are preferred including diethyl ether, diisopropyl ether, THF, etc.

To achieve high yields of the desired product, it is important to add the hydrogen chloride to the reaction medium in a controlled manner, in particular, during the initial stages of the reaction of the nitrite with the 4-HAP. During the initial stages of the reaction, hydrogen chloride is provided in amounts which favor the nitrosation of the 4-HAP as shown in equation (V). Thus, until such tie as one mole of nitrite has been reacted for every mole of 4-HAP in the reaction medium, hydrogen chloride should be provided in amounts of about 0.10 to no more than 6 moles per every mole of 4-HAP initially present. Preferably, the HCl addition should be limited to about 0.10 to 3 moles per mole of 4-HAP during reaction of the first equivalent of nitrite. At such time as the first equivalent of nitrite is reacted, hydrogen chloride can then be provided in an amount of at least 1 mole per mole of 4-HAP initially present in the reaction medium. Although no maximum limit to the amount of HHCl has yet been found to be critical during the second stage of the reaction or chlorination stage, extreme excesses of HCl should be avoided for economic reasons and to reduce the chance of forming undesirable side products. Preferably not more than 3 moles of HCl per 1 mole of starting 4-HAP are used during reaction. It is further possible to add all of the HCl to the reaction medium initially so long as the amount of HCl does not exceed 6 moles per mole of 4-HAP. The HCl can be added to the reaction medium as a liquid dissolved in an appropriate solvent or as a gas which is sparged through the reaction medium. It has been found that if hydrogen chloride is added to the reaction medium in large amounts such as by continual sparging from the initial stages of the reaction, yield of the α-chloro-α-oximino-4-hydroxyacetophenone is drastically reduced and the increased formation of various side products results.

Reaction temperatures may vary, but typically, during the initial stages of the reaction as described above, temperatures ranging from about −10° to 0° C. are used while during the chlorination stage subsequent to the initial nitrosation stage of the reaction, temperatures of about 0° to 20° C. may be used. The initial stage o the reaction generally will take from about 1 minute to about 2 hours while the second stage subsequent to the reaction of the one equivalent of nitrite will take from about 10 minutes to about one hour to produce the final product.

After completion of the reaction, the reaction mixture is then dissolved in a vehicle for the α-chloro-α-oximino-4-hydroxyacetophenone. A suitable vehicle is poly(ethylene glycol) M.W. 200. Subsequently, the solvent for the 4-HAP and the isopropyl alcohol formed from reaction are stripped off at elevated temperatures yielding a biocide composition comprising from about 10 to 20% of the product in the vehicle solution.

The following examples are for the purpose of illustrating the invention only and should not be construed to strictly limit the invention as claimed herein to only the embodiments shown.

EXAMPLE 1

A three neck 250 mL round bottom flask was equipped with a reflux condenser, an addition funnel and a gas sparge tube The flask was charged with 5 g 4-hydroxyacetophenone and 100 mL of diethyl there. The flask contents were stirred and cooled to 1° C. The addition funnel was charged with 12 mL of isopropyl nitrite which was then added to the flask slowly (ca. 5 min). The contents of the flask were sparged with HCl for 15 minutes. During this time the temperature peaked at 26° C. The HCl sparging was stopped and the contents of the flask were allowed to stand stirring at 1° C. for 30 minutes. The contents were then HCl sparged for 5 minutes and again allowed to stand stirring at 1° C. for 1 hr. The cooling bath was removed and the contents allowed to warm to room temperature and stand stirring for 2 hrs. The orange solution was then poured into a 1-L round bottom flask containing 42 g of PEG 200 and the flask rinsed with 5 mL of diethyl ether. The ether and isopropyl alcohol were stripped off on a rotovap at 90° C. yielding a yellow oil. HPLC analysis indicated that the oil was 13.1% alpha-chloro-alpha-oximino-4-hydroxyacetophenone. This translates into an 89% yield.

EXAMPLE 2

This example represents a comparison with the process of the present invention as described in Example 1.

A 250 mL round bottom flask was equipped with a reflux condenser, an addition funnel and a gas sparge tube. The flask was charged with 5 g 4-hydroxyacetophenone and 100 mL diethyl ether. The addition funnel was charged with 13 mL of isopropyl nitrite and 50 mL of diethyl ether. The flask contents were stirred and HCl sparged for 15 minutes. Next the contents of the addition funnel were added dropwise over a 1.5 hr period while continually sparging with HCl. The HCl sparging and stirring were continued for 2 hrs. The stirring and sparging were stopped and the contents allowed to stand for 2 hrs. The greenish yellow solution was poured into a round bottom flask which contained 42 g of PEG 200. The diethyl ether and isopropyl alcohol were then stripped off on a rotovap at 90° C. yielding a yellow oil (49 g). HPLC analysis of the oil indicated that it was 5.6% alpha-chloro-alpha-oximino-4-hydroxyacetophenone. This translates into a 38% yield.

EXAMPLE 3

A 250 mL round bottom flask was equipped with a reflux condenser, a thermowell and an addition funnel that interchanged with a gas sparge tube. The flask was charged with 60 mL of diethyl ether. The contents were then cooled to 0° C. and sparged with HCl for 15 minutes and then 15 g of 4-hydroxyacetophenone added. The addition funnel was charged with 36 mL of isopropyl nitrite and 40 mL of diethyl ether. The contents of the addition funnel were added over a 1 hr period during which time the temperature did not exceed 6° C. The contents of the flask were then sparged with HCl for 5 minutes and allowed to stand stirring at 0° for 1.5 hr. The ice bath was removed and the contents allowed to stand stirring at room temperature for 1.5 hr. The contents were poured into a 1-L round bottom flask which contained 125 g PEG 200. The reaction flask was rinsed with 25 mL of diethyl ether and added to the 1-L round bottom. The diethyl ether and isopropyl alcohol were removed on the rotovap at 90° C. yielding 148.6 g of yellow brown oil. HPLC analysis indicated that the oil was 12.2% alpha-chloro-alpha-oximino-4-hydroxyacetophenone. This translates into an 83% yield.

EXAMPLE 4

A three neck 250 mL round flask was equipped with a reflux condenser, a thermowell and an addition funnel. The flask was charged with 5 g 4-hydroxyacetophenone, 60 mL isopropyl ether and 23 mL of a 27% HCl/isopropyl ether solution. The addition funnel was charged with 12 mL isopropyl nitrite and 20 mL isopropyl ether. The contents of the flask were stirred and cooled to 0° C. The contents of the addition funnel were then added slowly over a 35 minute period. The temperature did not exceed 5° C. The contents were allowed to stand stirring in the ice bath for 1 hr. The contents were then warmed to room temperature and allowed to stand stirring for 1.5 hr. The contents were poured into a 1-L round bottom flask which contained 42 g of PEG 200. The isopropyl ether and isopropyl alcohol were removed on the rotovap at 90° C. yielding an oil (50 g). HPLC analysis indicated that the oil was 12.5% alpha-chloro-alpha-oximino-4-hydroxyacetophenone. This translates into an 85% yield.

EXAMPLE 5

A three neck 250 mL ground bottom flask was equipped with a reflux condenser, a thermowell and an addition funnel. The flask was charged with 15 g 4-hydroxyacetophenone, 16 mL isopropyl ether and 84 mL of a 20.6% HCl/isopropyl ether solution. The addition funnel was charged with 35 mL isopropyl nitrite. The contents of the flask were stirred and cooled to 0° C. The contents of the addition funnel were then added slowly over a 70 minute period. The temperature did not exceed 13° C. The contents were allowed to stand stirring in the ice bath for 2 hr. The contents were then warmed to room temperature and allowed to stand stirring for 2 hr. The contents were poured into a 1-L round bottom flask which contained 125 g of PEG 200 and the reaction flask rinsed with 25 mL of isopropyl ether. The isopropyl ether and isopropyl alcohol were removed on the rotovap at 90° C. yielding an oil (148 g). HPLC analysis indicated that the oil was 10% alpha-chloro-alpha-oximino-4-hydroxyccetophenone. This translates into a 68% yield.

EXAMPLE 6

A 3-neck round bottom flask was equipped with a reflux condenser, an addition funnel, and a HCl gas bubble tube. The flask was charged with 5 g. of 4-HAP and 75 mL of diethyl ether. The addition funnel was charged with 13 mL of crude isopropyl nitrite and 50 mL of diethyl ether. The contents of the flask were stirred and sparged with HCl for 15 minutes. The contents of the addition funnel were added in small portions, over a period of 1½ hours. Stirring and sparging continued with HCl for 2 hours. The contents of the flask were allowed to stand for an additional 2 hours. The mixture, a greenish-yellow solution containing a few crystals, were poured into a tared 500 mL round bottom flask containing 42 g. of PEG 200. The material was rotovaped for 2 hours, yielding 49 g. of a yellow oil. The material was submitted for LC analysis. The weight percent of CHIMP by LC was 5.6%. This translates into a 37.5% yield of CHIMP in the 49 g. sample.

EXAMPLE 7

A 250 mL 3 neck round bottom flask was equipped with a reflux condenser, an addition funnel, and a tube for bubbling HCl. The flask was charged with 5 g. of 4-HAP and 75 mL of diethyl ether. The addition funnel was charged with 15 mL of crude isopropyl nitrite and 25 mL of diethyl ether. The contents of the flask were stirred and sparged with HCl for 5 minutes. The contents of the addition funnel were added in small portions over a period of 1½ hours while continuing the HCl sparge. After addition, the contents were orange brown. The contents of the flask were allowed to stand stirring with HCl sparging for 2 hours. The contents were a light yellow green at the end of this time. The stirring and sparging were stopped and the flask contents were allowed to stand for 2 hours. The light yellow green solution was poured into a tared 500 mL round bottom flask containing 42 g. of PEG 200. The flask with 25 mL of diethyl ether was rinsed and the diethyl ether was poured into the 500 mL flask. The diethyl ether and isopropyl alcohol were removed by rotovaping (90° C., 28 in Hg vac) for 2 hours yielding 48.9 g. of yellow oil. The sample was submitted for LC and titration analysis. The sample was determined to be 7.4 wt. % CHIMP by LC analysis. This translates into a 49.4% yield of CHIMP in the 48.9 g. solution.

EXAMPLE 8

A 250 mL 3 neck ground bottom flask was equipped with a reflux condenser, addition funnel and an HCl sparge tube. The flask was charged with 15 g. 4-HAP and 70 mL methylene chloride. The addition funnel was charged with 43 mL of 90% n-butyl nitrite. The 4-HAP/methylene chloride slurry was stirred and HCl was bubbled through the slurry for 5 minutes forming a dark yellow solution. Stirring and HCl sparging continued while adding the contents of the addition funnel in small portions over a period of 1 and ½ hours. Addition of the first portion turned the solution dark brown. The product was dark green-brown at the end of tee addition. The contents of the flask were stirred and allowed to sparge for 1 and ½ hours. Stirring and sparging were stopped and the flask contents were allowed to stand for 1 and ½ hours. The dark green brown solution, containing some solids, were poured into a tared 1-liter round bottom flask containing 132 g. of PEG 200. The reaction flask was rinsed with 50 mL of methylene chloride and poured into the round bottom. The methylene chloride and butyl alcohol (90 degrees C at 28 inches Hg) were rotovaped off for 2 hours, yielding 154.5 g. of light green brown oil. The sample was submitted for LC and titration analysis. The sample was determined to be 3.3 wt. % CHIMP by LC analysis. This translates into a 23.2% yield of CHIMP in the 154.5 g. solution.

EXAMPLE 9

A 250 mL 3 neck round bottom flask was equipped with an addition funnel, an HCl sparge tube and a reflux condenser. The flask was charged with 15 g. 4-HAP and 70 mL diethyl ether. The addition funnel was charged with 43 mL of 90% n-butyl nitrite and 40 mL of diethyl ether. The slurry was stirred and HCl sparged in the reaction flask for 5 minutes. The solids dissolved, forming a tan solution. The stirring and sparging was continued. The contents of the addition funnel were added in small portions over a 1 hour period. The first portion turned the solution dark brown. After the contents of addition funnel were added, the solution turned dark green brown Sparging and stirring continued for 2 hours. Sparging and stirring were stopped and the dark green brown solution containing some solids were allowed to stand for 1 and ½ hours. The dark green brown solution which contained some solids were poured into a tared 1-liter round bottom flask containing 132.4 g. of PEG 200. The reaction flask with 40 mL of diethyl ether was rinsed and poured into the 1-liter flask. The diethyl ether and n-butyl nitrite were removed on the rotovap (90° C. at 28 in Hg) for 2 and ½ hours. 154.9 g. of a light green brown oil were yielded. The sample was submitted for LC and titration analysis. The small was determined to be 3.3 wt. % by LC analysis. This translates into a yield of 23.2% CHIMP in the 154.0 g. solution.

EXAMPLE 10

A three neck 2-L bottom flask was equipped with a reflux condenser, a thermowell, and an addition funnel. The flask was charged with 100 grams 4-HAP, 750 mL THF and 20 mL 25% HCl/THF solution. The reactor contents were stirred and cooled (externally) to −10° C. The addition funnel was charged with 250 mL include isopropyl nitrite. The isopropyl nitrite was slowly (ca. 1 hr) added keeping the temperature between −10° to 0° C. 240 mL 25% HCl/THF solution was then added slowly (ca. 1 hr) keeping the temperature between 0° C. to 10° C. The reactor contents were allowed to warm to room temperature (ca. 25° C.) and stand stirring overnight. The next day the reactor contents were poured into a 3-L round bottom flask containing 740 grams PEG 200 The isopropanol/THF was evaporated by rotary evaporator at 90° C. under vacuum (ca. 25" Hg). The desired product was residue (914 g with a titrometric assay of 14.9% CHIMP). This translated into a 92.8% yield.

What is claimed is:

1. A process for producing α-chloro-α-oximino-4-hydroxyacetophenone comprising adding an alkyl nitrite to a reaction medium containing 4-hydroxyacetophenone for reaction therewith, providing in the reaction medium from about 0.1 to 6 moles of hydrogen chloride for each mole of 4-hydroxyacetophenone initially present in said reaction medium while at least 1 mole of alkyl nitrite for every mole of said 4-hydroxyacetophenone is reacted, subsequent to the reaction of said at least one mole of alkyl nitrite, providing in said reaction medium at least 1 mole of hydrogen chloride per 1 mole of 4-hydroxyacetophenone initially charged to the reaction medium, and recovering α-chloro-α-oximino-4-hydroxyacetophenone.

2. The process of claim 1 wherein not more than about 3 moles of HCl per mole of 4-hydroxyacetophenone initially charged to the reaction medium are provided in the reaction medium during reaction of said at least one mole of alkyl nitrite.

3. The process of claim 1 wherein subsequent to the reaction of said at least one mole of alkyl nitrite, sparging hydrogen chloride gas through said reaction medium.

4. The process of claim 1 wherein said hydrogen chloride is provided as a liquid dissolved in a solvent in said reaction medium.

5. The process of claim 3 wherein hydrogen chloride is provided in said reaction medium in an amount of less than 1 mole of hydrogen chloride per mole of 4-hydroxyacetophenone initially present in said reaction medium until said at least one mole of alkyl nitrite is reacted.

6. The process of claim 2 wherein said 4-hydroxyacetophenone is provided to said reaction medium dissolved in a solvent.

7. The process of claim 6 wherein subsequent to reaction, the product is recovered by dissolving the reaction medium in a vehicle solvent for the α-chloro-α-oximino-4-hydroxyacetophenone and the dissolved reaction medium heated to volatilize the solvent for said 4-hydroxyacetophenone and alkyl alcohol formed during reaction.

8. The process of claim 7 wherein said carrier solvent comprises polyethylene glycol.

9. A process for producing α-chloro-α-oximino-4-hydroxyacetophenone comprising adding isopropyl nitrite to a reaction medium containing 4-hydroxyacetophenone for reaction therewith, providing in the reaction medium from about 0.1 to 6 moles of hydrogen chloride for each mole of 4-hydroxyacetophenone initially present in said reaction medium while at least 1 mole of isopropyl nitrite for every mole of said 4-hydroxyacetophenone is reacted, subsequent to the reaction of said at least one mole of isopropyl nitrite, providing in said reaction medium at least 1 mole of hydrogen chloride per 1 mole of 4-hydroxyacetophenone initially charged to the reaction medium, and recovering α-chloro-α-oximino-4-hyroxyacetophenone.

10. The process of claim 9 wherein not more than about 3 moles of HCl per mole of 4-hydroxyacetophenone initially charged to the reaction medium is added during the reaction of said at least one mole of nitrite.

11. The process of claim 9 wherein subsequent to the reaction of said at least one mole of isopropyl nitrite, sparging hydrogen chloride gas through said reaction medium.

12. The process of claim 9 wherein said hydrogen chloride is provided as a liquid dissolved in a solvent into said reaction medium.

13. The process of claim 11 wherein hydrogen chloride is added to said reaction medium in an amount of less than 1 mole of hydrogen chloride per mole of 4-hydroxyacetophenone present in said reaction medium until said at least one mole of isopropyl nitrite is reacted.

14. The process of claim 9 wherein said 4-hydroxyacetophenoneiis provided to said reaction medium dissolved in a solvent.

15. The process of claim 14 wherein subsequent to reaction, the products are dissolved in a carrier solvent for the α-chloro-α-oximino-4-hydroxyacetophenone and the dissolved product heated to volatilize the solvent for said 4-hydroxyacetophenone and isopropyl alcohol formed during reaction.

16. The process of claim 15 wherein said carrier solvent comprises polyethylene glycol.

17. The process of claim 12 wherein the solvent for the hydrogen chloride is an ether.

18. The process of claim 17 wherein the solvent for the hydrogen chloride is tetrahydrofuran.

19. The process of claim 17 wherein said 4-hydroxyacetophenone is provided to said reaction medium dissolved in a solvent.

20. The process of claim 19 wherein the solvent for said 4-hydroxy acetophenone is tetrahydrofuran.

* * * * *